(12) United States Patent
Kyeong (10) Patent No.: US 11,944,477 B2
(45) Date of Patent: Apr. 2, 2024

(54) DIAGNOSTIC DEVICE FOR COMPANION ANIMAL

(71) Applicant: AURACARE CO., LTD., Yongin-si (KR)

(72) Inventor: Hyeon Tae Kyeong, Seoul (KR)

(73) Assignee: AURACARE CO., LTD., Yongin-si (KR)

(*) Notice: Subject to any disclaimer, the term of this patent is extended or adjusted under 35 U.S.C. 154(b) by 388 days.

(21) Appl. No.: 17/348,955

(22) Filed: Jun. 16, 2021

(65) Prior Publication Data

US 2021/0307710 A1    Oct. 7, 2021

Related U.S. Application Data

(63) Continuation of application No. PCT/KR2019/017903, filed on Dec. 17, 2019.

(30) Foreign Application Priority Data

Dec. 20, 2018 (KR) .................. 10-2018-0166591

(51) Int. Cl.
*A61B 6/00* (2006.01)
*A61B 6/04* (2006.01)

(52) U.S. Cl.
CPC .............. *A61B 6/4452* (2013.01); *A61B 6/04* (2013.01); *A61B 6/563* (2013.01); *A61B 2503/40* (2013.01)

(58) Field of Classification Search
CPC ...... A61B 2090/372; A61B 2017/0027; A61B 2034/2048; A61B 5/224; A61B 5/06;
(Continued)

(56) References Cited

U.S. PATENT DOCUMENTS

2006/0058645 A1   3/2006  Komistek et al.
2016/0278724 A1   9/2016  Papaioannou
(Continued)

FOREIGN PATENT DOCUMENTS

JP    04-040942 A    2/1992
JP    2006-340965 A   12/2006
(Continued)

OTHER PUBLICATIONS

International Search Report of PCT/KR2019/017903 dated Mar. 27, 2020.

*Primary Examiner* — Don K Wong
(74) *Attorney, Agent, or Firm* — Dinsmore & Shohl LLP; Yongsok Choi, Esq.

(57) ABSTRACT

An apparatus for diagnosing a companion animal with radiation is provided. The apparatus includes a radiation irradiation unit configured to generate the radiation and irradiate the radiation toward a diagnosis object; a detector disposed to face the radiation irradiation unit and configured to detect the radiation irradiated from the radiation irradiation unit; a driving unit configured to adjust positions of the radiation irradiation unit and the detector; and a communication unit configured to communicate with an external device in a wireless manner. The driving unit adjusts the positions of the radiation irradiation unit and the detector such that the diagnosis object is located between the radiation irradiation unit and the detector, and the radiation irradiation unit irradiates the radiation toward the diagnosis object when the diagnosis object is located between the radiation irradiation unit and the detector.

4 Claims, 5 Drawing Sheets

(58) Field of Classification Search
CPC ........... A61B 3/10; A61B 5/0077; A61B 5/24; A61B 5/339
See application file for complete search history.

(56) References Cited

U.S. PATENT DOCUMENTS

| | | |
|---|---|---|
| 2018/0028136 A1 | 2/2018 | Manetti et al. |
| 2018/0055467 A1 | 3/2018 | Cox et al. |
| 2020/0250860 A1* | 8/2020 | Son ..................... G06T 11/008 |

FOREIGN PATENT DOCUMENTS

| | | | |
|---|---|---|---|
| JP | 2018-183395 A | 11/2018 | |
| KR | 101105624 B1 | 1/2012 | |
| KR | 101793844 B1 | 11/2017 | |
| WO | 2006042211 A2 | 4/2006 | |
| WO | WO-2015054466 A1 * | 4/2015 | ............. A61B 6/032 |

* cited by examiner

DIAGNOSTIC DEVICE FOR COMPANION ANIMAL

CROSS-REFERENCE TO RELATED APPLICATIONS

This application is a continuation of PCT/KR2019/017903 filed on Dec. 17, 2019 which claims priority to Korean Patent Application No. 10-2018-0166591 filed on Dec. 20, 2018, the entire contents of which are herein incorporated by reference.

TECHNICAL FIELD

The present disclosure relates to a companion animal diagnosis apparatus, more particularly, to a companion animal diagnosis apparatus capable of diagnosing a companion animal using radiation without anesthetizing the companion animal.

BACKGROUND

In recent years, the perception of the companion animal is changing to a family member who shares emotion with the human being rather than a pet just living together with the human being. In addition, as the number of single-person households increases recently, the number of households which raise the companion animals to soothe loneliness is increasing.

As described above, with the change in perception of the companion animal and the increase in the number of households which raise companion animals, demand for diagnosis and treatment of disease or injury of the companion animal is also on the rise.

Meanwhile, like the human being, the companion animal may be precisely diagnosed by a radiation diagnosis machine, such as an X-ray, a computerized tomography (CT) or the like. However, such a radiation diagnosis machine is very costly and requires a wide installation space. This makes it difficult for a typical animal hospital to operate the machine. Further, in order to prevent the companion animal from moving during radiography for diagnosis, the companion animal needs to be anesthetized. This requires an expert for anesthesia operation and an additional recovery space. Furthermore, some of the companion animals may be hardly anesthetized due to disease, aging, or the like.

Therefore, there is a need for the development of a diagnosis apparatus which can operate at a low cost in a compact structure and can perform radiography without an additional anesthesia process.

SUMMARY

The present disclosure is made in view of this problem, and an object of the present disclosure is to provide a companion animal diagnosis apparatus capable of performing a radiation diagnosis without anesthetizing a companion animal.

A companion animal diagnosis apparatus according to one embodiment of the present disclosure comprises: a radiation irradiation unit configured to generate radiation and irradiate the radiation toward a diagnosis object; a detector disposed to face the radiation irradiation unit and configured to detect the radiation irradiated from the radiation irradiation unit; a driving unit configured to adjust positions of the radiation irradiation unit and the detector; and a communication unit configured to communicate with an external device in a wireless manner. The driving unit is configured to adjust the positions of the radiation irradiation unit and the detector such that the diagnosis object is located between the radiation irradiation unit and the detector, and the radiation irradiation unit is configured to irradiate the radiation toward the diagnosis object when the diagnosis object is located between the radiation irradiation unit and the detector.

The companion animal diagnosis apparatus according to one embodiment of the present disclosure may further comprise a sensor configured to sense a position of the diagnosis object. Furthermore, the radiation irradiation unit may be configured to automatically irradiate the radiation toward the diagnosis object when the sensor senses that the diagnosis object is located between the radiation irradiation unit and the detector.

According to one embodiment of the present disclosure, the radiation irradiation unit may be configured to irradiate the radiation toward the diagnosis object based on a signal relating to a radiation irradiation received from the external device through the communication unit.

According to one embodiment of the present disclosure, the radiation irradiation unit and the detector may be provided on respective rails and may be configured to move along the respective rails by the driving unit.

According to a companion animal diagnosis apparatus of one embodiment of the present disclosure, it is possible to perform radiography while a companion animal freely moves and thus performs radiation diagnosis without anesthetizing the companion animal.

DETAILED DESCRIPTION OF THE PRESENT INVENTION

Hereinafter, preferred embodiments of the present disclosure will be described in detail with reference to the appended drawings to such an extent that the present disclosure can be readily practiced by one of ordinary skill in the art.

Detailed descriptions of parts irrelevant to the present disclosure will be omitted for the purpose of more clearly describing the present disclosure. Throughout the specification, the same components will be described using like reference numerals. In addition, it should be understood that specific shapes, configurations, and characteristics described in the specification may be modified in various embodiments without departing from the spirit and scope of the prevent disclosure, and positions or arrangements of individual components may be modified without departing from the spirit and scope of the prevent disclosure.

Throughout the present specification, when a component is referred to as being "connected" to another component, the component can be directly connected to another component, or can be connected to another component by intervening yet another component there between.

Configuration of a Companion Animal Diagnosis System

Figure 1:
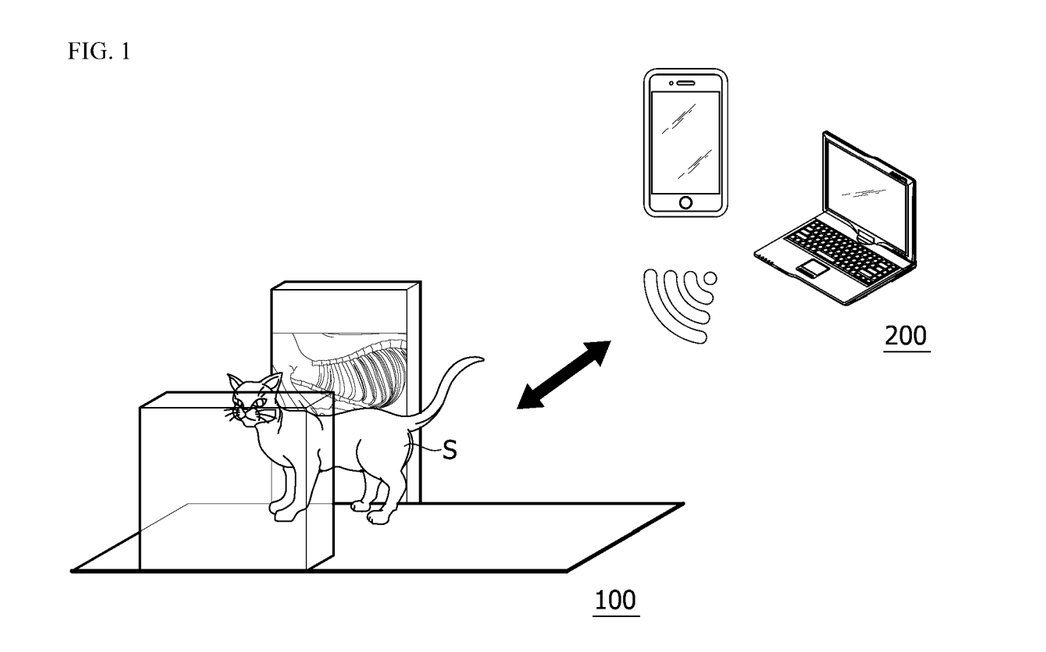
FIG. 1 illustrates a companion animal diagnosis system according to one embodiment of the present disclosure.

FIG. 1 illustrates a companion animal diagnosis system according to one embodiment of the present disclosure.

Referring to FIG. 1, the companion animal diagnosis system according to one embodiment of the present disclosure includes a companion animal diagnosis apparatus 100 and a user terminal 200 connected to the companion animal diagnosis apparatus 100 in a wireless manner and configured to control the companion animal diagnosis apparatus 100.

The companion animal diagnosis apparatus 100 according to one embodiment of the present disclosure is an apparatus for diagnosing a companion animal S through radiography and is manufactured in a small size unlike a radiation diagnosis apparatus for diagnosing a human being. Thus, the companion animal diagnosis apparatus 100 can be installed in a narrow space, thereby being utilized in a typical animal hospital. This makes it possible to more easily diagnose disease or injury of the companion animal S.

According to one embodiment of the present disclosure, the companion animal diagnosis apparatus 100 may be configured to be controlled by the user terminal 200. The user terminal 200 may be a digital equipment having an arithmetic capacity, which incorporates a memory means and a microprocessor, such as a notebook computer, a desktop computer, a smartphone, a tablet, a personal digital assistant (PDA), a web pad or the like. A user may control an operation of the companion animal diagnosis apparatus 100 through an application program installed in the user terminal 200. Further, the user may input and manage information on the companion animal S using the user terminal 200 or check diagnosis results obtained by the companion animal diagnosis apparatus 100. For example, the user may input information on the type, weight, size and the like of the companion animal S using the user terminal 200, set diagnosis parameters such as a radiation intensity, an irradiation time and the like corresponding to the information to operate the companion animal diagnosis apparatus 100, and check the diagnosis results through radiography.

As described above, since the companion animal diagnosis apparatus 100 according to one embodiment of the present disclosure is controlled by the user terminal 200 connected to the companion animal diagnosis apparatus 100 in a wireless manner, it is possible to diagnose the companion animal S through the radiography during free movement of the companion animal without giving the companion animal S a sense of discomfort.

Configuration of the Companion Animal Diagnosis Apparatus

Figure 2:
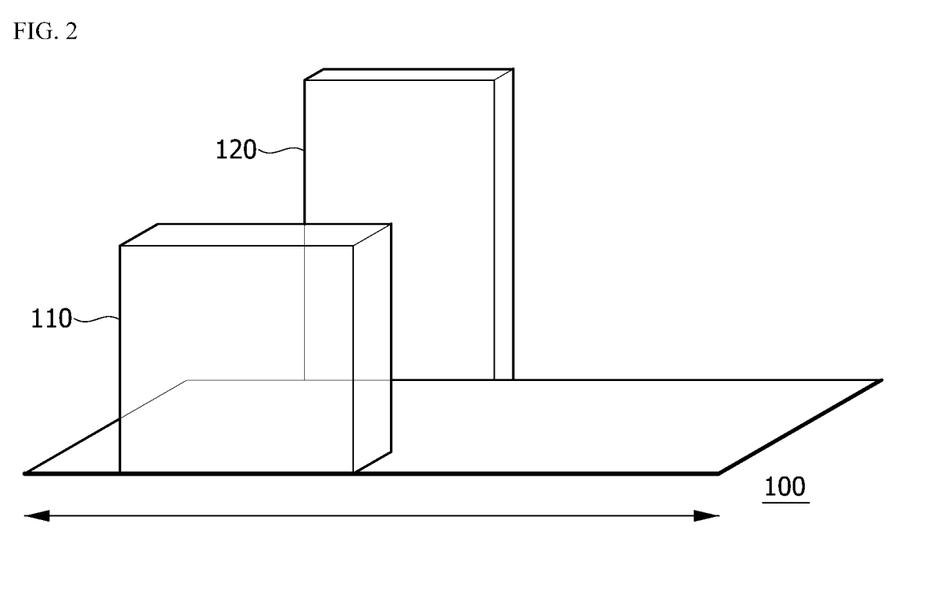
FIG. 2 is a perspective view of a companion animal diagnosis apparatus according to one embodiment of the present disclosure.
Figure 3:
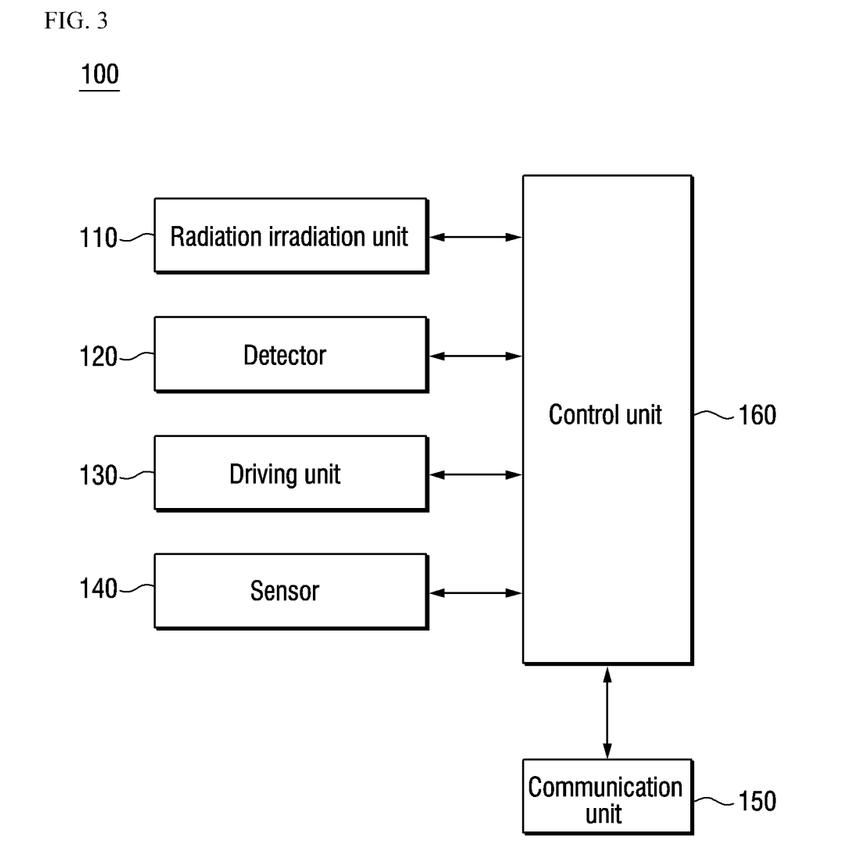
FIG. 3 is a view schematically illustrating an internal configuration of the companion animal diagnosis apparatus according to one embodiment of the present disclosure.

FIG. 2 is a perspective view of the companion animal diagnosis apparatus according to one embodiment of the present disclosure, and FIG. 3 is a view schematically illustrating an internal configuration of the companion animal diagnosis apparatus according to one embodiment of the present disclosure.

Referring to FIGS. 2 and 3, the companion animal diagnosis apparatus 100 according to one embodiment of the present disclosure may include a radiation irradiation unit 110, a detector 120, a driving unit 130, a sensor 140, a communication unit 150, and a control unit 160.

The radiation irradiation unit 110 of the companion animal diagnosis apparatus 100, which is a unit configured to generate radiation and irradiate the same toward the companion animal S as a diagnosis object, may include a radiation source configured to generate the radiation, a collimator configured to adjust a dispersion angle and an irradiation range of the radiation, a filter configured to adjust an intensity of the radiation, and the like. According to one embodiment of the present disclosure, the intensity and the irradiation range of the radiation may be adjusted according to the type, weight, size and the like of the companion animal S as a diagnosis object.

The detector 120 of the companion animal diagnosis apparatus 100 is configured to detect the radiation irradiated from the radiation irradiation unit 110, and is disposed to face the radiation irradiation unit 110 as shown in FIG. 2.

A space where the companion animal S as a diagnosis object can freely move is formed between the radiation irradiation unit 110 and the detector 120.

According to one embodiment of the present disclosure, the radiation irradiation unit 110 and the detector 120 may be disposed on respective rails (not shown). The rails provide movement paths through which the radiation irradiation unit 110 and the detector 120 move respectively. Thus, the radiation irradiation unit 110 and the detector 120 may move along the respective rails while facing each other by the driving unit 130 to be described later.

As described above, the radiation irradiation unit 110 and the detector 120 are moved by the driving unit 130 at positions facing each other. To this end, the radiation irradiation unit 110 and the detector 120 may be driven as a unit in a state in which they are connected to each other through an additional structure formed on upper or lower portions of the radiation irradiation unit 110 and the detector 120. In some embodiments, the radiation irradiation unit 110 and the detector 120 may move in parallel while moving independently of each other and keeping the positions facing each other.

In the present embodiment, the radiation irradiation unit 110 and the detector 120 are described to be provided on the bottom of an open place, but the present disclosure is not limited thereto. For example, an elongated bed may be provided like in a conventional radiotherapy machine, and a radiation irradiation unit and a detector may be provided on both sides of the bed. Alternatively, a cage for limiting a movement range of the radiation irradiation unit and the detector may be provided such that the companion animal S moves only in the space defined between the radiation irradiation unit and the detector.

According to one embodiment of the present disclosure, the operation of the radiation irradiation unit 110 may be controlled by the user terminal 200 described above. For example, when a radiation irradiation signal is input by the user terminal 200, the radiation irradiation unit 110 irradiates the radiation. In this case, the intensity, the irradiation time, the irradiation range and the like of the radiation irradiated from the radiation irradiation unit 110 may be set through the user terminal 200.

According to one embodiment of the present disclosure, the operation of the detector 120 may be controlled by the user terminal 200 like in the radiation irradiation unit 110. When the radiation irradiated from the radiation irradiation unit 110 is detected, the detector 120 may transmit respective data to the user terminal 200.

The driving unit 130 of the companion animal diagnosis apparatus 100 is configured to perform a function of adjusting positions of the radiation irradiation unit 110 and the detector 120. For example, in the case in which the radiation irradiation unit 110 and the detector 120 are provided on the respective rails, the driving unit 130 may drive the radiation irradiation unit 110 and the detector 120 such that they move in one direction of the rails while facing each other.

The driving unit 130 may include a motor, and a roller that is rotated by the motor and connected to the rails, and is configured to displace the positions of the radiation irradiation unit 110 and the detector 120 by travelling the rails connected to the roller with the driving of the motor. However, the present disclosure is not limited thereto. It will be apparent to a person skilled in the art that various known techniques may be applied to the driving unit 130 in moving the radiation irradiation unit 110 and the detector 120.

According to one embodiment of the present disclosure, the driving unit 130 may also be controlled by the user terminal 200. For example, when information on positions of the radiation irradiation unit 110 and the detector 120 is input to the user terminal 200, the driving unit 130 may move the radiation irradiation unit 110 and the detector 120 to the respective positions.

The companion animal diagnosis apparatus 100 according to one embodiment of the present disclosure may further include the sensor 140 in addition to the radiation irradiation unit 110, the detector 120, and the driving unit 130.

The sensor 140 of the companion animal diagnosis apparatus 100 may perform a function of sensing the presence of the companion animal S as a diagnosis object or a position of the companion animal S. The sensor 140 may include a sensor provided in the space between the radiation irradiation unit 110 and the detector 120 to sense a load and detect the position of the companion animal S, or may include an infrared sensor provided in the radiation irradiation unit 110 or the detector 120 to determine whether the companion animal S is located between the radiation irradiation unit 110 and the detector 120. In addition, various known sensors may be provided to sense the presence of the companion animal S, or the position of the companion animal S.

According to one embodiment of the present disclosure, the companion animal diagnosis apparatus 100 may operate the radiation irradiation unit 110 and the driving unit 130 based on the position information of the companion animal S obtained by the sensor 140.

For example, when the companion animal S is sensed to be located between the radiation irradiation unit 110 and the detector 120 by the sensor 140, the respective information may be transmitted to the user terminal 200 through the communication unit 150 (to be described later) such that the radiation can be irradiated by the operation of the user. Alternatively, when the companion animal S is sensed to be located between the radiation irradiation unit 110 and the detector 120 by the sensor 140, the respective information may be transmitted to the radiation irradiation unit 110 such that the radiation irradiation unit 110 automatically irradiates the radiation.

In some embodiments, based on the position of the companion animal S sensed by the sensor 140, the driving unit 130 may be operated to move the radiation irradiation unit 110 and the detector 120 to the point where the companion animal S is located.

The communication unit 150 of the companion animal diagnosis apparatus 100 may perform a function of transmitting or receiving signals and data between the companion animal diagnosis apparatus 100 and the user terminal 200. The communication unit 150 may be configured by a short-range wireless communication module including a Wi-Fi and a Bluetooth Low Energy (BLE), and may be connected to the user terminal 200 in a wireless manner.

The control unit 160 of the companion animal diagnosis apparatus 100 is configured to control the flow of signals and data between the radiation irradiation unit 110, the detector 120, the driving unit 130, the sensor 140, and the communication unit 150. That is, the control unit 160 according to one embodiment of the present disclosure controls the flow of signals and data inside the companion animal diagnosis apparatus 100, the flow of signals and data to/from the outside of the companion animal diagnosis apparatus 100, thereby controlling each component to execute a task uniquely assigned thereto.

The companion animal diagnosis apparatus 100 according to one embodiment of the present disclosure has a simplified structure as described above. Therefore, it is possible to reduce the size of the apparatus and manufacture the apparatus at a low cost. This makes it possible for a typical animal hospital to utilize a radiation machine for diagnosing a companion animal and provide a service of diagnosing disease or injury of the companion animal at a lower cost.

In addition, the companion animal diagnosis apparatus 100 according to one embodiment of the present disclosure has an open structure and may perform the radiography on the companion animal S freely moving in the space between the radiation irradiation unit 110 and the detector 120. This eliminates a need to anesthetize the companion animal S for diagnosis. Therefore, not only an expert for anesthesia of the companion animal S or an additional recovery space but also the time required for anesthesia and recovery are not necessary. This reduces the total diagnosis time. In particular, it is also possible to diagnose a companion animal that may be hardly anesthetized due to aging or the like. This significantly increases the application range of the radiation diagnosis.

Figure 4A:
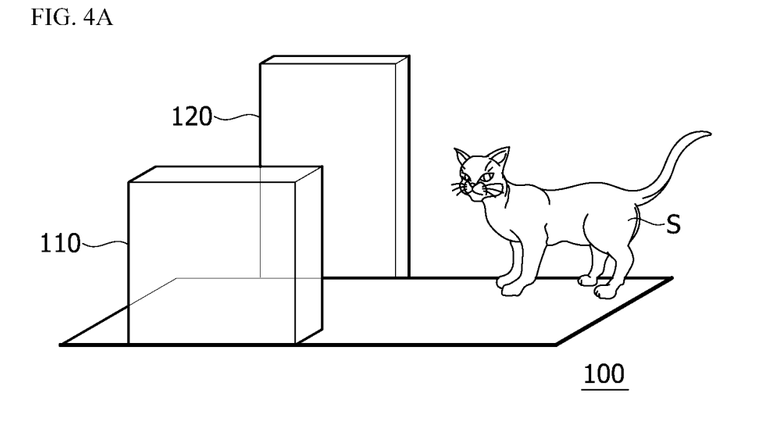
FIG. 4A is a view illustrating an operational aspect of the companion animal diagnosis apparatus according to one embodiment of the present disclosure.
Figure 4B:
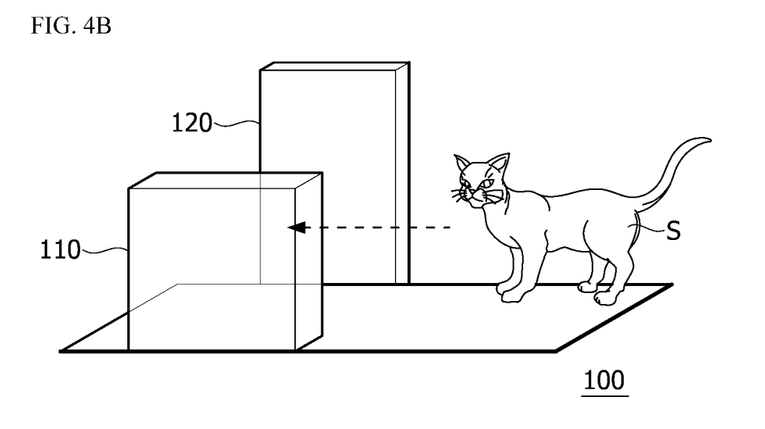
FIG. 4B is a view illustrating an operational aspect of the companion animal diagnosis apparatus according to one embodiment of the present disclosure.
Figure 4C:
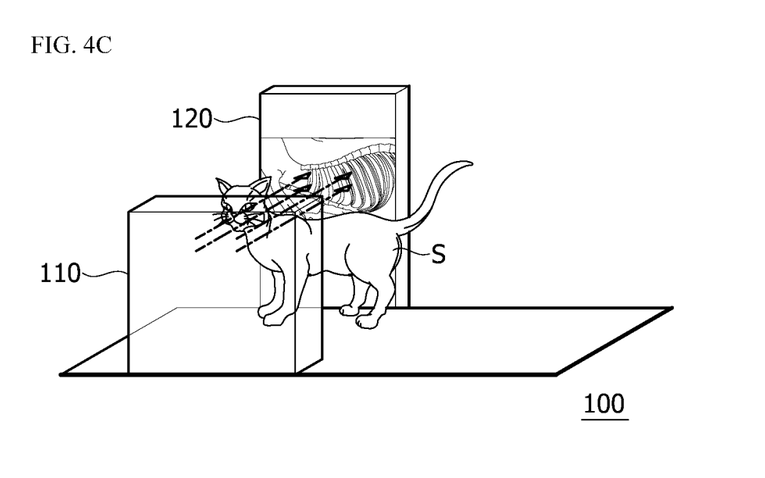
FIG. 4C is a view illustrating an operational aspect of the companion animal diagnosis apparatus according to one embodiment of the present disclosure.
Figure 5A:
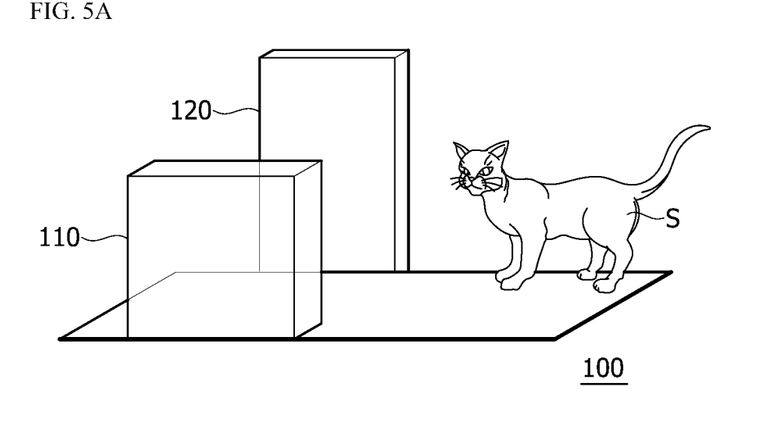
FIG. 5A is a view illustrating another operational aspect of the companion animal diagnosis apparatus according to one embodiment of the present disclosure.
Figure 5B:
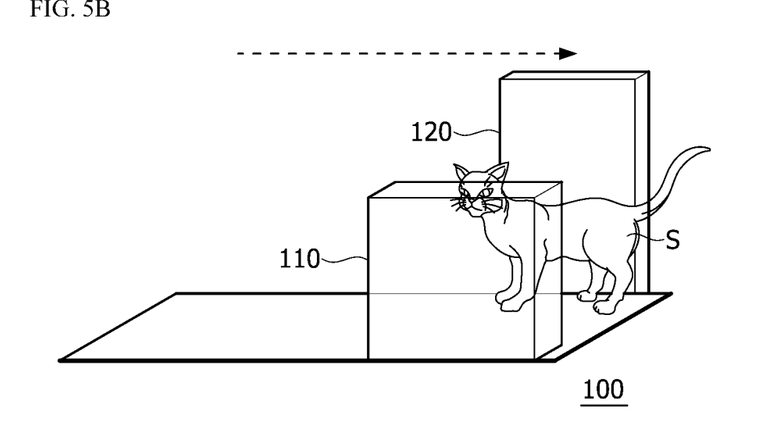
FIG. 5B is a view illustrating another operational aspect of the companion animal diagnosis apparatus according to one embodiment of the present disclosure.
Figure 5C:
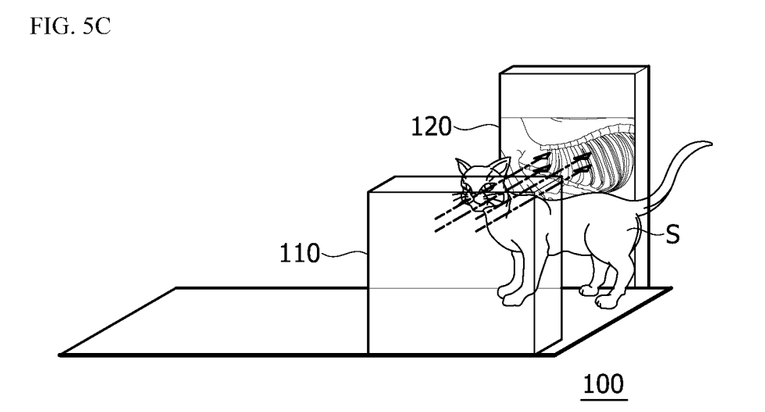
FIG. 5C is a view illustrating another operational aspect of the companion animal diagnosis apparatus according to one embodiment of the present disclosure.

Companion Animal Diagnosis Method Using the Companion Animal Diagnosis Apparatus FIGS. 4 and 5 are views showing operational aspects of the companion animal diagnosis apparatus according to one embodiment of the present disclosure. Hereinafter, a companion animal diagnosis method using the companion animal diagnosis apparatus according to one embodiment of the present disclosure will be described with reference to FIGS. 4 and 5.

Referring first to FIGS. 4A through 4C, the companion animal S as a diagnosis object is located in the space formed between the radiation irradiation unit 110 and the detector 120 in order to diagnose whether the companion animal S has disease or injury (shown in FIG. 4A). The companion animal S can move freely in the space defined between the radiation irradiation unit 110 and the detector 120 (shown in FIG. 4B). When the companion animal S is located between the radiation irradiation unit 110 and the detector 120 during the movement, the radiation irradiation unit 110 irradiates radiation toward the companion animal S (shown in FIG. 4C). The radiation irradiated from the radiation irradiation unit 110 penetrates the companion animal S and is sensed by the detector 120. The detector 120 transmits information on the sensed radiation to the user terminal 200 through the communication unit 150 such that the user can check the respective diagnosis results.

A diagnosis method illustrated in FIGS. 5A through 5C is different from the diagnosis method described with reference to FIGS. 4A through 4C in that the positions of the radiation irradiation unit 110 and the detector 120 can be adjusted. Specifically, when the companion animal S is located in the space defined between the radiation irradiation unit 110 and the detector 120 (shown in FIG. 5A), the radiation irradiation unit 110 and the detector 120 may be moved to a place where the companion animal S is located by the driving unit 130 (shown in FIG. 5B). When the companion animal S is located between the radiation irradiation unit 110 and the detector 120, the movement of the radiation irradiation unit 110 and the detector 120 is paused, and subsequently, the radiation irradiation unit 110 irradiates the radiation toward the companion animal S (see in FIG. 5C). Similarly, the radiation irradiated from the radiation irradiation unit 110 penetrates the companion animal Sand is sensed by the detector 120. The detector 120 transmits information on the sensed radiation to the user terminal 200 such that the user can check the respective diagnosis results.

In the companion animal diagnosis method using the companion animal diagnosis apparatus 100 according to one embodiment of the present disclosure, the user is described to control the radiation irradiation unit 110, the driving unit 130, and the like through the user terminal 200. In some embodiments, the user may operate the radiation irradiation unit 110 or the driving unit 130 based on the position information of the companion animal S sensed by the sensor 140. In this case, the radiation irradiation for diagnosis may be performed through the user terminal 200 or may be automatically performed.

While the present disclosure has been described in the foregoing by way of embodiments and drawings which are defined with specific matters such as specific components and the like, this is only the one provided to aid in a more general understanding of the present disclosure, and the present disclosure is not limited to the above embodiments, and various modifications and variations can be made from the substrate to those skilled in the art to which the present disclosure pertains.

Accordingly, the spirit of the present disclosure should not be defined as limited to the embodiments described above, and all that have been equivalently or equivalently modified with the claims to be described below, as well as those to be within the scope of the spirit of the present disclosure.

What is claimed is:

1. An apparatus for diagnosing a companion animal with radiation, comprising:
a radiation irradiation unit configured to generate the radiation and irradiate the radiation toward a diagnosis object;
a detector disposed to face the radiation irradiation unit and configured to detect the radiation irradiated from the radiation irradiation unit;
a driving unit configured to adjust positions of the radiation irradiation unit and the detector;
a sensor configured to sense a position of the diagnosis object; and
a communication unit configured to communicate with an external device in a wireless manner,
wherein the radiation irradiation unit comprises a radiation source, a collimator for adjusting a dispersion angle and an irradiation range of the radiation, and a filter for adjusting an intensity of the radiation, and is configured to adjust the intensity and the irradiation range of the radiation according to the diagnosis object,
wherein the radiation irradiation unit and the detector are provided on both sides of an elongated bed and configured to move along the elongated bed,
wherein the sensor is provided in a space between the radiation irradiation unit and the detector to sense a load and detect the position of the diagnosis object,
wherein the driving unit adjusts the positions of the radiation irradiation unit and the detector based on the position of the diagnosis object obtained by the sensor such that the diagnosis object is located between the radiation irradiation unit and the detector, and the radiation irradiation unit irradiates the radiation toward the diagnosis object when the diagnosis object is located between the radiation irradiation unit and the detector, and
wherein via the external device, diagnosis parameter including a radiation intensity and an irradiation time is set in accordance with information of the diagnosis object and an operation of the apparatus is controlled, and diagnosis results are checked.

2. The apparatus of claim 1, wherein the radiation irradiation unit is configured to automatically irradiate the radiation toward the diagnosis object when the sensor senses that the diagnosis object is located between the radiation irradiation unit and the detector.

3. The apparatus of claim 1, wherein the radiation irradiation unit is configured to irradiate the radiation toward the diagnosis object based on a signal relating to a radiation irradiation received from the external device through the communication unit.

4. The apparatus of claim 1, wherein the radiation irradiation unit and the detector are provided on respective rails and are configured to move along the respective rails by the driving unit.

* * * * *